United States Patent

Newcomb et al.

(10) Patent No.: US 6,451,828 B1
(45) Date of Patent: Sep. 17, 2002

(54) SELECTIVE INHIBITION OF GLUTAMINASE BY BIS-THIADIAZOLES

(75) Inventors: Robert W. Newcomb, deceased, late of Palo Alto; by Marcelle Newcomb, legal representative, Whittier, both of CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/927,207

(22) Filed: Aug. 10, 2001

Related U.S. Application Data

(60) Provisional application No. 60/224,395, filed on Aug. 10, 2000.

(51) Int. Cl.⁷ .............................. A61K 31/433
(52) U.S. Cl. ..................................... 514/363
(58) Field of Search ......................... 514/363

(56) References Cited

U.S. PATENT DOCUMENTS

| | | | |
|---|---|---|---|
| 5,158,976 A | 10/1992 | Rosenberg | 514/561 |
| 5,552,427 A | 9/1996 | Matsutani et al. | 514/398 |

FOREIGN PATENT DOCUMENTS

| WO | 99/09825 | * | 3/1999 |
|---|---|---|---|

OTHER PUBLICATIONS

Newcomb, R. et al., "Increased Production of Extracellular Glutamate by the Mitochondrial Glutamise following Neuronal Death", *J. Biol. Chem.* 272(17):11276–82, Apr. 25, 1997.

\* cited by examiner

*Primary Examiner*—Phyllis G. Spivack
(74) *Attorney, Agent, or Firm*—LeeAnn Gorthey; Perkins Coie LLP

(57) ABSTRACT

Compounds are disclosed which efficiently inhibit glutaminase but which have no effect, at higher levels, on various mechanistically and functionally related enzymes. The compounds, which are useful for neuroprotection and in treatment of hepatic encephalopathy, have the general formula I:

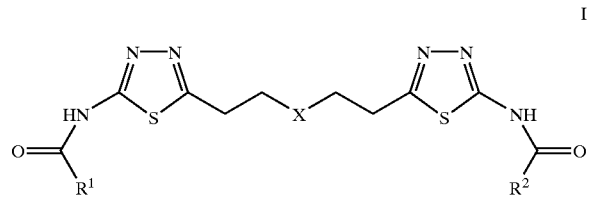

as defined further herein.

15 Claims, 6 Drawing Sheets

SELECTIVE INHIBITION OF GLUTAMINASE BY BIS-THIADIAZOLES

This application claims the benefit of U.S. patent application Ser. No. 60/224,395 filed Aug. 10, 2000, which is incorporated in its entirety herein by reference.

FIELD OF THE INVENTION

The present invention relates to selective and potent. inhibition of the enzyme glutaminase. Compounds are disclosed which efficiently inhibit glutaminase but which have no effect, at higher levels, on various mechanistically and functionally related enzymes. The compounds are useful for neuroprotection and in treatment of hepatic encephalopathy.

REFERENCES

Ahluwalia, G. S. et al., Metabolism and action of amino acid analog anti-cancer agents. *Pharmac. Ther.* 46:243–271 (1990).

Almeida, A. F. et al., Maximal activities of key enzymes of glutaminolysis, glycolysis, krebs cycle and pentose-phosphate pathway of several tissues in mature and aged rats. *Int. J. Biochem.* 21:937–940 (1989).

Conjeevaram, H. S. et al., Reversal of behavioral changes in rats subjected to portocaval shunt with oral neomycin therapy. *Hepatology* 19:1245–1250 (1993).

Cooper, A. J. L., Ammonia metabolism in mammals: Inter-organ relationships, in *Cirrhosis, Hyperammonemia, and Hepatic Encephalopathy*, Eds. Grisola, S., and Felipo, V., Plenum, N.Y. (1994).

Di Pierro, D. et al., *Analytical Biochemistry* 231:407–412 (1995).

Dugan, L. L. et al., Glia modulate the response of murine cortical neurons to excitotoxicity: Glia exacerbate AMPA neurotoxicity. *J. Neurosci.* 15:4545–4555 (1995).

Hawkins, R. A. and Mans, A. M, Brain metabolism in hepatic encephalopathy and hyperammonemia, in *Cirrhosis, Hyperammonemia, and Hepatic Encephalopathy*, Grisola, S., and Felipo, V., Eds., Plenum, N.Y., pp. 13–19 (1994).

Kvamme, E. et al., Glutaminase from mammalian tissue. *Meth. Enzymol.* 113:241–256 (1985).

Kerouel, R. and Aminot, A., *Marine Chemistry* 57:265–275 (1997).

Lo, E. H., Pierce, A. R., Matsumoto, K., Kano, T., Evans, C., Newcomb, R., Alterations in K+ evoked profiles of neurotransmitter and neuromodulator amino acids after focal ischemia-reperfusion. *Neuroscience* 83:449–458 (1998).

Mousseau, D. D. and Butterworth, R. F., Current theories on the pathogenesis of hepatic encephalopathy. *Proc. Soc. Exp. Biol.* 206(4):329–344 (1994).

Oppong, K. N. W. et al., Oral glutamine challenge in cirrhotics pre- and post-liver transplantation: A psychometric and analyzed EEG study. *Hepatology* 26:870–876 (1997).

Seiler, N. et al., Enhanced endogenous ornithine concentrations protect against tonic seizures and coma in acute ammonia intoxication. *J. Pharmacol. Toxicol.* 72:116–123 (1993).

Schousboe, A. et al., Preparation of primary cultures of mouse (rat) cerebellar granule cells, in *A Dissection and Tissue Culture Manual of the Nervous System*, Alan R. Liss, Inc., New York (1989).

Shapiro, R. A. et al., Covalent interaction of L-2-amino-4-oxo-5-chloropentanoic acid with rat renal phosphate-dependent glutaminase. *J. Biol. Chem.* 253:7086–7090 (1978).

Shapiro, R. A. et al., Inactivation of rat renal phosphate-dependent glutaminase with 6-diazo-5-oxo-L-norleucine. Evidence for interaction at the glutamine binding site. *J. Biol. Chem.* 254(8):2835–8 (1979).

Stauch, S. et al., Oral L-omithine-L-aspartate therapy of chronic hepatic encephalopathy: Results of a placebo-controlled double-blind study. *J. Hepatol.* 28:856–864 (1998).

Wood, P., Roles of CNS macrophages in neurodegeneration, in *Neuroinflammation Mechanisms and Management*, Wood, P. L., Ed., Humana, Totowa, N.J., pp 1–59 (1997).

Zea Longa, E. et al., Reversible middle artery occlusion without craniectomy. *Stroke* 20: 84–91 (1989).

BACKGROUND OF THE INVENTION

Glutaminase is currently recognized as the most significant glutamine utilizing enzyme present in mammalian central nervous tissue (e.g., the brain and spinal cord). The enzyme catalyzes the conversion of glutamine and water to glutamate, with the production of ammonia.

Following ischemic insult or other traumatic injury to neuronal cells, a number of biochemical changes occur in neuronal tissue surrounding the injured region, including a rise in the extracellular concentration of the excitatory neurotransmitter glutamate. This high concentration of glutamate is believed to be an important factor in delayed neuronal death, in which the ischemic lesion increases approximately 2-fold over a period of time 2–72 hours following the initial ischemic insult. It is believed that this elevated glutamate level exacerbates the primary insult, possibly by acting at excitatory glutamate receptors, and that at least some of the excess glutamate results from enzymatic conversion of glutamine to glutamate by glutaminase.

The maximal activity of glutaminase in the brain is 5–10 $\mu$mol/min/g (Alameida et al., 1989). This activity corresponds to a capacity for generating glutamate at a concentration of 5–10 mM each minute, a rate far in excess of the 5–10 $\mu$M IC$_{50}$ for toxicity of glutamate on isolated neurons (Dugan et al., 1995). Therefore, it is apparent that only a very minor fraction of the glutaminase present in the brain needs to be active in a pathological circumstance in order to cause damage. Accordingly, inhibition of glutaminase has been reported as a neuroprotective treatment following ischemic injury (see e.g. Newcomb, PCT Pubn. No. WO 99/09825).

Inhibition of glutaminase may also be used for treatment of hepatic encephalopathy. This condition can arise from chronic liver damage, such as chronic forms of viral hepatitis. Portal blood from the intestine is shunted around the damaged liver, entering the circulation directly. The resulting exposure of the brain to elevated concentrations of blood ammonia produces neurologic symptoms ranging from intellectual impairment and psychiatric symptoms to coma. Several million people are affected to some degree (Hawkins et al.). Current treatments are based on lowering blood ammonia, either by decreasing ammonia generation in the gut, e.g. by treatment with the antibiotic neomycin (Conjeevaram et al.), or by biochemical manipulation of ammonia excretion. For example, the efficacy of ammonia fixation by the urea cycle can be increased by increasing the concentration of ornithine, which is accomplished by inhibiting ornithine amino transferase with a compound such as 5-fluoromethylornithine (Seiler et al.). The use of L-ornithine-L-aspartate has also been reported (Stauch et al.). These treatments, while useful, suffer from toxicity (neomycin) or only partial effectiveness (ornithine compounds).

The role of glutaminase in regulation of blood ammonia is described in Cooper et al. and Oppong et al., and includes the hydrolysis of glutamine to glutamate and ammonia by glutaminase in the intestine. Thus, hepatic encephalopathy could be treated by selective inhibition of glutaminase in intestinal tissue.

To date, no glutaminase inhibitors have been reported that are both potent and specific for glutaminase. Known inhibitors, such as 6-diazo-5-oxo-L-norleucine ("DON"; Shapiro et al. 1979) and L-2-amino-4-oxo-5-chloropentanoic acid ("chloroketone"; Shapiro et al. 1978; see also Rosenberg, U.S. Pat. No. 5,156,976), also inhibit a variety of glutamine utilizing enzymes, such as amidotransferases (Ahluwahia et aL, 1990).

SUMMARY OF THE INVENTION

The present invention includes, in one aspect, a method of selectively inhibiting glutaminase in a cell or tissue, comprising administering to the cell or tissue an effective amount of a compound of formula I:

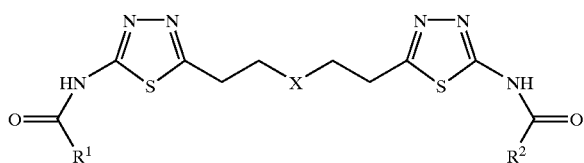

where

X is sulfur or oxygen, and $R^1$ and $R^2$ are independently selected from the group consisting of lower alkyl, lower alkoxy, aryl, and —$(CH_2)_n$-aryl, where n is 0 or 1, and "aryl" is a monocyclic aromatic or heteroaromatic group, having ring atoms selected from the group consisting of carbon, nitrogen, oxygen, and sulfur, and having at most three non-carbon ring atoms, which group may be unsubstituted or substituted with one or more substituents selected from halogen, lower alkyl, lower alkoxy, amino, lower alkyl amino, amino(lower alkyl), or halo(lower alkyl). $R^1$ and $R^2$ may be the same or different; for ease of preparation, $R^1$ and $R^2$ are the same.

Preferably, X is sulfur. In one embodiment, each of $R^1$ and $R^2$ is —$(CH_2)_n$-aryl as defined above. The aryl group may be carbocyclic, e.g. where each of $R^1$ and $R^2$ is phenyl or benzyl, where the ring is unsubstituted or substituted as recited above. Preferred compounds include those in which the ring is unsubstituted or substituted with lower alkyl or lower alkoxy. This group includes exemplary compounds in which each of R and R is benzyl, each of $R^1$ and $R^2$ is p-methoxy phenyl, or each of $R^1$ and $R^2$ is m-tolyl. Compounds with heterocyclic aryl groups include those in which each of $R^1$ and $R^2$ is 2-thiophenyl or each of $R^1$ and $R^2$ is 2-furanyl. Compounds in which $R^1$ and $R^2$ are non-aryl include those in which each of $R^1$ and $R^2$ is lower alkoxy, such as ethoxy, or where each of $R^1$ and $R^2$ is lower alkyl, e.g. t-butyl.

In one embodiment, the tissue is neuronal tissue which has been subjected to ischemia, physical trauma, or a neurodegenerative or neuropsychiatric disorder. Alternatively, the tissue is intestinal tissue, particularly in a subject suffering from hepatic encephalopathy.

These and other objects and features of the invention will become more fully apparent when the following detailed description of the invention is read in conjunction with the accompanying drawings.

DETAILED DESCRIPTION OF THE INVENTION

I. Definitions

Figure 1:
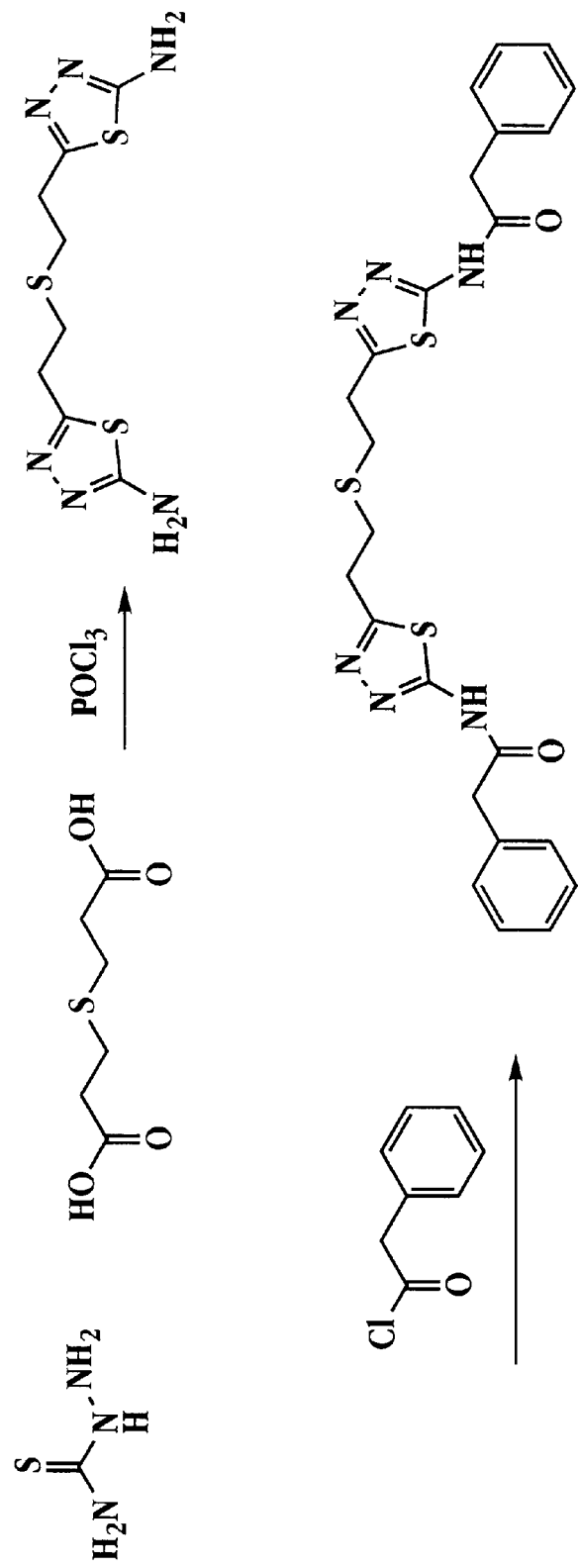
FIG. 1 shows a representative synthetic scheme for preparing the compounds of the invention.

The terms below have the following meanings unless indicated otherwise. "Alkyl" refers to a fully saturated acyclic monovalent radical containing carbon and hydrogen, which may be branched or a straight chain. Examples of alkyl groups are methyl, ethyl, n-butyl, n-heptyl, and iso-propyl. "Lower alkyl", a subset of this class, refers to alkyl having one to six carbon atoms, and more preferably one to four carbon atoms.

"Aralkyl" refers to a monovalent alkyl radical substituted with an aryl group, as defined herein, e.g. a benzyl group (—$CH_2C_6H_5$).

A "pharmaceutically acceptable salt" of a compound described herein refers to the compound in protonated form with one or more anionic counterions, such as chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. Hydrochloride salts are a preferred group. The term also encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethylammonium, bis(2-hydroxyethyl) ammonium, phenylethylbenzylammonium, dibenzylethylenediammonium, and the like. Such salts may be formed by substitution of ionizable groups onto, for example, phenyl rings in group $R^1$ or $R^2$, which can be useful for increasing solubility or for reducing membrane permeability, if desired.

The terms "neuronal cell damage", "damage to neuronal cells", and "cell injury" refer to conditions in which the integrity of a neuronal cell has been compromised. This condition may be a result of an ischemic event, a concussive traumatic event, a degenerative event, or the like.

The terms "hypoxic", "hypoxia", "ischemic" and "ischemia", as used herein, refer to conditions in which eukaryotic cells, particularly neuronal cells, are exposed to oxygen concentrations that are at least 50% less than a normal range of oxygen tension required for normal growth and maintenance of such cells in culture or in vivo.

II. Glutaminase Inhibiting Compounds

The selective glutaminase inhibiting compounds of the invention have the general formula I

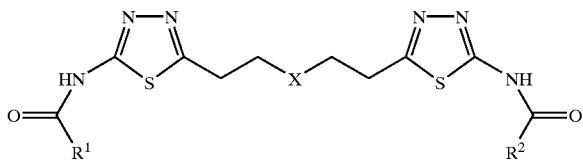

where X is sulfur or oxygen, and $R^1$ and $R^2$ are independently selected from the group consisting of lower alkyl, lower alkoxy, aryl, and —$(CH_2)_n$-aryl, where n is 0 or 1. As used herein, "aryl" refers to a monocyclic aromatic or heteroaromatic group, having ring atoms selected from the group consisting of carbon, nitrogen, oxygen, and sulfur, and having at most three non-carbon ring atoms. The aryl group may be unsubstituted, or it may be substituted with one or more substituents selected from halogen, lower alkyl, lower alkoxy, amino, lower alkyl amino, amino(lower alkyl), and halo(lower alkyl). Preferably, each ring has at most three substituents, more preferably at most two, and most preferably one or no substituents. While $R^1$ and $R^2$ are typically identical for ease of synthesis, $R^1$ and $R^2$ may be different.

In preferred embodiments, X is sulfur, and each of $R^1$ and $R^2$ is —$(CH_2)_n$-aryl, as defined above. In one embodiment, each of $R^1$ and $R^2$ is phenyl or benzyl, where the ring is unsubstituted or substituted with lower alkyl or lower alkoxy. Preferably, the substituent is a single meta or para substituent. This group includes compounds designated herein as SNX-1770 (unsubstituted benzyl), 1853 (unsubstituted phenyl) and 1832 (p-methoxy phenyl). Other preferred embodiments include compounds in which X is sulfur and the aryl group is furanyl (e.g. compound 1836) or thiophenyl (e.g. compound 1837).

Compounds of the invention may exist in other forms depending on solvent, pH, temperature, and other variables known to practitioners skilled in the art. For example, equilibrium forms may include tautomeric forms. The compounds may be chemically modified to enhance specific biological properties, such as biological penetration, solubility, oral availability, stability, metabolism, or excretion. The compounds may also be modified to prodrug forms, such that the active moiety results from the action of metabolic or biochemical processes on the prodrug.

The compounds can be prepared by reaction of a diacid, such as shown in FIG. 1, with two moles of thiosemicarbazide to give a bis(aminothiadiazole), followed by condensation with the appropriate acid chloride(s) to give the desired $R^1$ and $R^2$ substituents. Any reactive substituents that may be present on the $R^1$ or $R^2$ groups may be protected, if necessary, and then deprotected according to methods well known in organic synthesis. Mixtures that may be produced when $R^1$ and $R^2$ are different are separated by known preparative methods, typically by chromatography. Preparation of the representative compound SNX-1770 (bis-2'-[5-(phenylacetamido)-1,3,4-thiadiazol-2-yl]ethyl sulfide) is illustrated in FIG. 1 and described in Example 1.

III. Glutaminase Inhibiting Properties

A. Screening Methods

The compounds of the invention were evaluated based on their ability to inhibit glutaminase in a cell-free assay (Example 2) and in rat brain membranes (Example 3), and to inhibit glutamate secretion by microglia (Examples 4–5). Effects of the compounds on glutaminase were confirmed by assays of different cell types, including neuronal cells and intestinal epithelial cells (Examples 6–7).

In general, glutaminase activity can be monitored by detecting production of either of the products of the reaction, i.e. glutamate or ammonia. Typically, glutamate production is measured, since ammonia is a product of a number of other biological reactions. Glutamate production can be measured by any of a number of standard methods known in the art, including chemical and chromatographic detection methods and coupled enzyme assays that utilize NADH and glutamate dehydrogenase. Extracellular glutamate concentrations can also be measured in vivo, using microdialysis methods known in the art. One suitable method for measuring glutamate is a microtiter-based two-step assay in which glutamate formed in the initial step is quantitatively deaminated by glutamate dehydrogenase to yield an equivalent amount of NADH (Kvamme et al., 1985), which can then be detected spectrophotometrically, as described in Example 2.

Specificity for glutaminase was evaluated at two levels. Compounds were evaluated for specific interactions with several thiol hydrolases (cathepsin B, caspase-9, calpain-1, and thrombin). These are cysteine proteases which are believed to function by a mechanisms similar to that of glutaminase. Compounds were also evaluated for effects on intracellular amino acids and nucleotides in CACO2 (intestinal epithelial) cells (Example 5), and for effects on amino acids in primary cultures of cerebellar neurons (granule cells) and astrocytes (Examples 6–7). These measurements reflect interactions with other glutamine utilizing enzymes involved in amino acid and nucleic acid biosynthesis and homeostasis. For example, a decrease in cytidine triphosphate (CTP) and an increase in uridine triphosphate (UTP) on treatment with DON (6-diazo-5-oxo-L-norleucine), a known nonselective antiglutamine affinity label, is indicative of inhibition of the activity of CTP synthetase, for which UTP is the substrate and CTP the product.

B. Cell Free Inhibition Assay

Compounds of formula I were tested for inhibition of human kidney glutaminase as described in Example 2. Results are given in Table 1 ($IC_{50}$=concentration required for 50% inhibition).

TABLE 1

| Cmpd No. SNX- | X = | $R^1 = R^2 =$ | $IC_{50}, \mu M$ |
|---|---|---|---|
| 1770 | S | benzyl | 0.19, 0.58 (two runs) |
| 1830 | S | phenyl | 1.06 |
| 1855 | S | o-methoxy phenyl | 4.90 |
| 1831 | S | m-tolyl | 1.13 |
| 1832 | S | p-methoxy phenyl | 0.46 |
| 1836 | S | 2-furanyl | 1.12 |
| 1837 | S | 2-thiophenyl | 0.39 |
| 1833 | S | methyl | 4.42 |
| 1851 | S | t-butyl | 1.65 |
| 1852 | S | ethoxy | 1.78 |
| 1853 | O | phenyl | 10.2 |

Compound 1770 gave similar results with enzyme expressed in human kidney cells ($IC_{50}$=0.18 $\mu$M) and with native enzyme ($IC_{50}$=0.16 $\mu$M).

C. Inhibition of Glutamate Secretion by Microglia

As described in Wood, glutamate efflux from microglia is dependent on the presence of added external glutamine. Experiments conducted in support of the present invention further showed that microglia do not significantly take up or metabolize added glutamate, and that glutamine dependent efflux is specific to glutamate, linear with time, and inhibited by the antiglutamine affinity label, 6-diazo-5-oxo-L-norleucine (DON). Therefore, the concentration of glutamate in the culture medium can be used directly as a measure of glutamate production by these cells.

Figure 4:
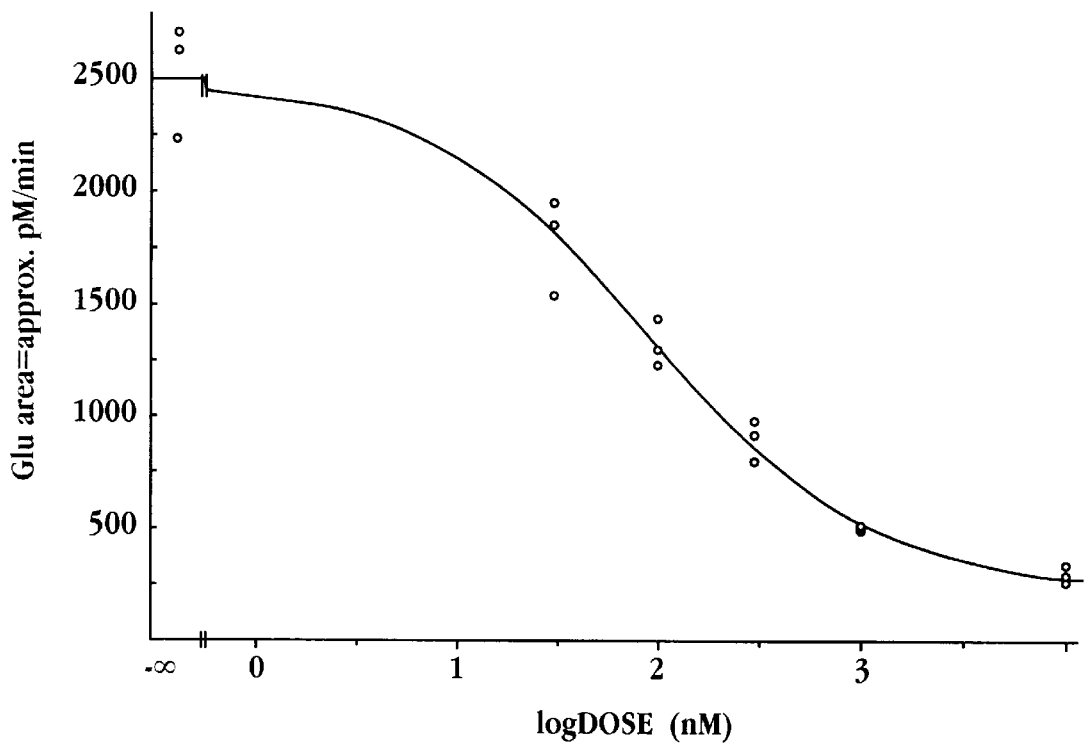
FIG. 4 shows inhibition of microglial glutamate secretion by SNX-1770.

In assaying the invention compounds, microglia (BV-2) cells were cultured using standard methods, as described in Example 4. On the day of the experiment, cells were incubated in glutamine free medium for 1 to 1.5 hours, then glutamine and test compounds, dissolved in glutamine free medium, were added. Aliquots were removed at 2 h and 4 h for glutamate analysis. As shown in FIG. 4, compound 1770 was able to inhibit glutamate efflux by microglia, giving an $IC_{50}$ value of 80–120 nM and ca. 85% inhibition at 10 µM.

D. Effect on Levels of Intracellular Glutamate in Cells

Figure 5A:
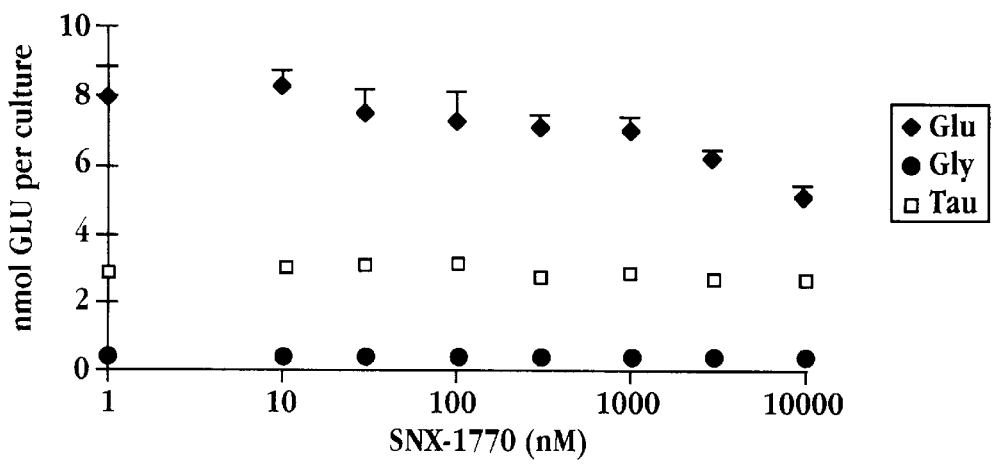
FIG. 5a shows the effect of SNX-1770 on intracelullar amino acids in intestinal epithelial cells (CACO2)
Figure 6A:
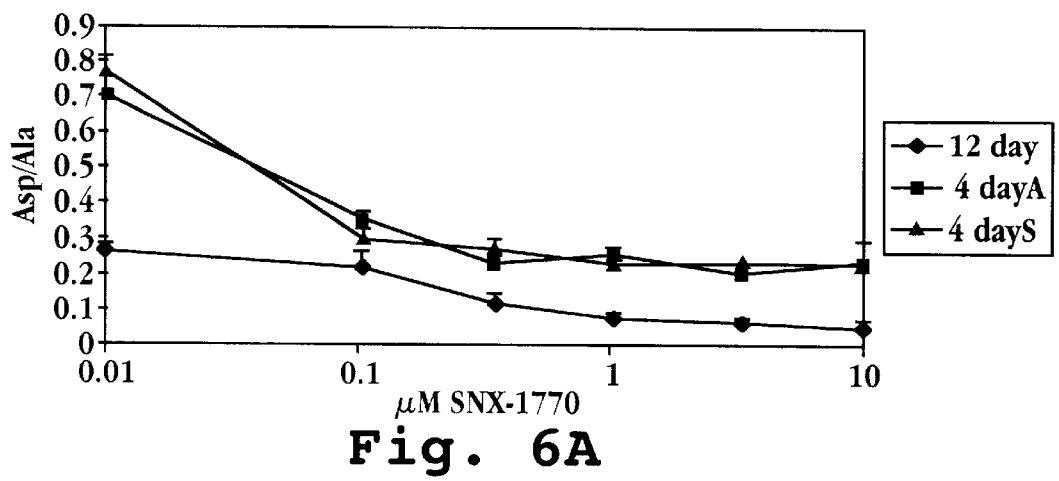
FIGS. 6a–c show dose response curves for lowering of intracellular glutamate, aspartate, and γ-amino butyric acid, respectively, in cerebellar granule cells (day 4 cultures) and astrocytes (day 12 cultures).
Figure 6B:
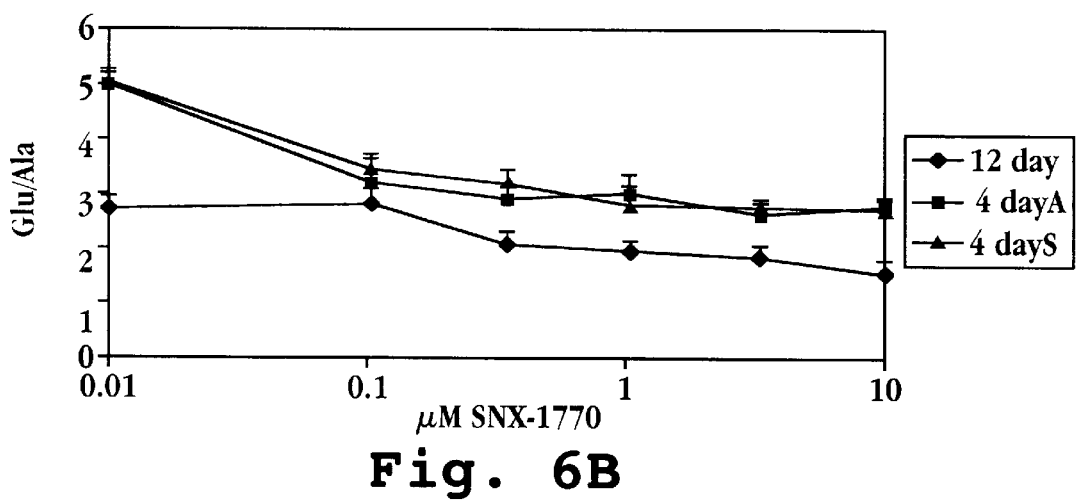

The effect of compound 1770 on intracellular amino acids was examined in CACO2 cells, granule cell neurons, and astrocytes, as described in Examples 6 and 7, below. Effects on glutamate are shown in FIGS. 5A and 6B. Compound 1770 caused a partial (~30%) and specific lowering of cellular glutamate in all cell types. $IC_{50}$ was determined to be 100–300 nM in primary cultures of astrocytes and 50–100 nM in primary cultures of cerebellar granule cells.

E. Specificity: Effects on Other Intracellular Amino Acids and Nucleotides

Figure 6C:
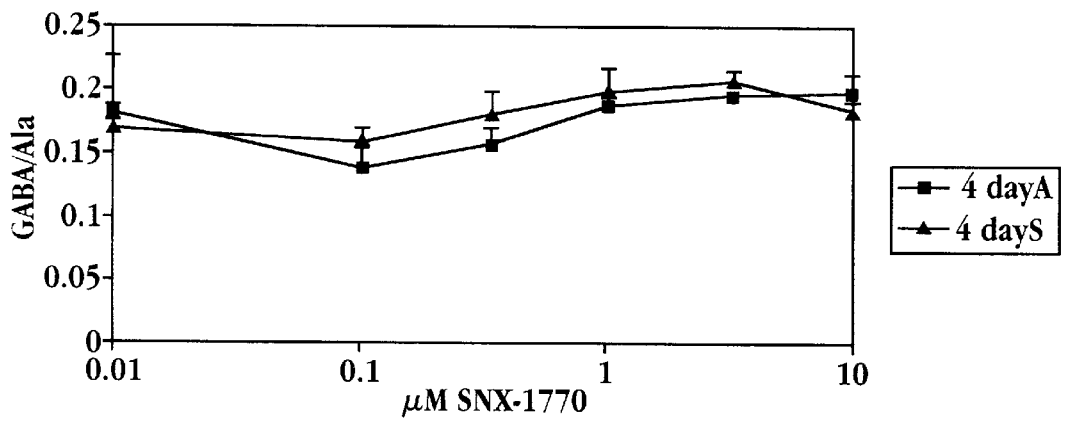

Compound 1770 had no effect at 10 µM on a variety of intracellular (non-glutamate) amino acids, including serine, glycine, arginine, alanine, and taurine, in cultured cerebellar neurons, astrocytes, and intestinal epithelial cells (Examples 6 and 7). This is illustrated in FIG. 5A for glycine and taurine. It also had no effect on cellular GABA (gamma-amino butyric acid) in granule cells at levels up to 10 µM, as shown in FIG. 6C. (In FIGS. 6A–C, data are expressed as the ratio of Glu, Asp, or GABA to Ala (neurons and astrocytes) or Ser (astrocytes). Amounts of Ala and Ser were shown not to change with SNX-1770.)

The remaining volume of the extracts was used for chromatographic determination of nucleic acids, as described in Di Pierro et al. This assay reflects the activity of a variety of glutamine amidotransferases, including CTP synthetase, which are mechanistically and functionally related to glutaminase.

CTP synthetase is a glutamine amidotransferase which synthesizes CTP by adding the amide nitrogen of glutamine to UTP. The enzyme is representative of a significant class of enzymes which possess glutaminase activity, and which are thought to work by a similar mechanism with the brain/kidney glutaminase, thus providing a stringent test of specificity.

Figure 5B:
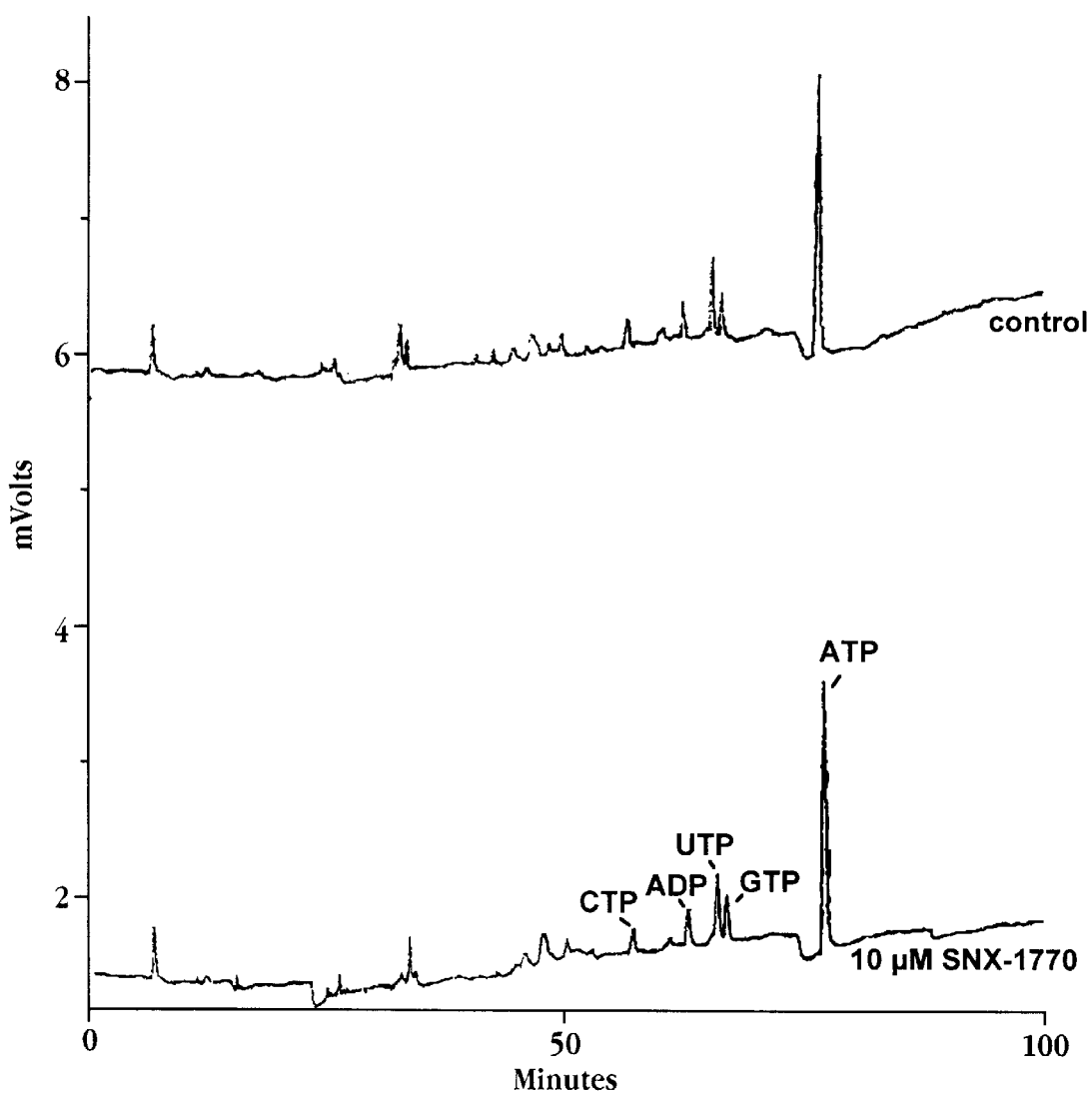
FIG. 5b shows the effect of SNX-1770 on nucleotides in intestinal epithelial cells (CACO2)

As shown in FIG. 5B, compound 1770 had no effect at 10 µM on intracellular nucleotides in intestinal epithelial cells (no detectable difference between test culture and control). Nor did it have any effect, at 30 µM, on a variety of mechanistically related enzymes, including thiol hydrolases, cathespin B, caspase 9, calpain 1, and thrombin (data not shown).

F. Effect on Ammonia Production by Intestinal Epithelial Cells

As stated above, selected glutaminase inhibition in intestinal tissue is expected to be beneficial in treating hepatic encephalopathy, by lowering blood ammonia levels. To test the effect of a compound on intestinal ammonia levels in vitro, intestinal epithelial cells (e.g. CACO2) are incubated in a balanced salt solution containing glucose and varying concentrations of the compound, with or without glutamine (about 2 mM). Following incubation, aliquots of medium were removed, brought to alkaline pH and placed in a closed vessel. The volatile ammonia is trapped in a strong acid, typically in the form of drop hanging at the top of the vessel, and, following neutralization, analyzed fluorometrically with o-phthaldialdehyde and sulfite, by a modification of the procedure of Kerouel and Aminot, 1997.

G. Cellular Permeability

Cellular permeability of SNX-1770 was demonstrated by its ability to lower intracellular amounts of glutamate and the biosynthetically related amino acids, at 30–100 nM in cultures of cerebellar neurons and astrocytes, and at 10 µM in cultures of intestinal epithelial cells.

H. Low Toxicity

Compound 1770 showed no toxicity up to 100 µM in cultured retinal epithelial cells, as measured by an assay of mitochondrial respiratory function. Administration of up to 60 mg/kg I.P. in rat was well tolerated.

I. Noncompetitive Inhibition

Glutaminase inhibition by the compounds of the invention is not competed by glutamine. The compounds bear no structural similarity to either glutamine or glutamate. They are therefore unlikely to interact with transporters, receptors or other enzymes that recognize glutamine or glutamate, which is consistent with their selectivity and low toxicity.

IV. Indications

A. Hepatic Encephalopathy

In accordance with the present invention, selective inhibition of glutaminase in intestinal tissue can be used to treat hepatic encephalopathy. As noted above, this is a condition in which blood from the intestine is shunted around a damaged liver, entering the circulation directly, and exposing the brain to elevated concentrations of blood ammonia. It has been reported that oral glutamine causes elevated blood ammonia in cirrhotics (Oppong et al. 1998). Inhibition of intestinal glutaminase may thus be directly therapeutic in hepatic encephalopathy.

Experiments with known inhibitors of glutamine-utilizing enzymes in neurons and astrocytes were used, in support of the invention, to establish that (1) glutaminase has a significant role in reversing the net incorporation of ammonia into glutamine by glutamine synthetase and that (2) steady state concentrations of intracellular amino acids in neurons and astrocytes can be used as a marker of nonselective inhibition of glutamine amidotransferase activity. Similar procedures can be used to establish other cell lines, such as intestinal epithelial cells, as model systems.

Cell based assays are used to measure the effect of inhibitors on ammonia production by an intestinal cell line exposed to glutamine, as described in Section IIIF above. Effects of glutaminase inhibitors on intracellular amounts of a variety of amino acids are also determined, as a measure of selectivity vs. glutamine amidotransferases. Compounds with attractive profiles are tested in one of the several animal models for hepatic encephalopathy. The most common employs surgical shunting of intestinal blood flow around the liver, or portacaval shunting (Hawkins et al; Conjeevaram et al.). Blood ammonia injections can be given for comparative purposes. Compound effects are evaluated biochemically, e.g. by measurement of blood ammonia and brain glutamine, or behaviorally, e.g. by observing restoration of locomotor activity (Hawkins et al.; Conjeevaram et al.).

Selective glutaminase inhibitors as described herein, administered orally or intraperitoneally, are expected to preferentially block ammonia generation by glutaminase in the intestine. Inhibition of glutaminase in tissue such as kidney, liver, and brain may provide additional lowering of blood levels of ammonia. In addition, it is thought that alterations in amino acid neurotransmission may underlie some of the neuropsychiatric symptoms of hepatic encephalopathy. Glutaminase is also involved in the biosynthesis of the brain neurotransmitter amino acids, glutamate, aspartate, and γ-amino butyrate. Accordingly, intravenous administration may also be effective for treatment of this disorder.

B. Neuroprotection

The compounds of the invention may be used to minimize damage to neuronal tissue, such as may occur in the brain as a result of cerebral ischemia, trauma, or degeneration. Ischemic damage to the central nervous system (CNS) may result from either global or focal ischemic conditions. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors. Ischemic diseases include cerebral ischemia, such as results from stroke, myocardial infarction, retinal ischemia, macular degeneration, and glaucoma.

Other sources of damage to central nervous tissue include various neurodegenerative diseases such as Alzheimer's disease (Kim et al., 1997), ALS and motor neuron degeneration (Greenlund et al., 1995), Parkinson's disease (Ghosh et al., 1994), peripheral neuropathies (Batistatou et al., 1993), Down's syndrome (Busciglio et al., 1995), age related macular degeneration (ARMD) (Hinton et al., 1998), Huntington's disease (Goldberg et al., 1996), spinal muscular atrophy (Liston et al., 1996), and HIV encephalitis (Lazdins et al., 1997).

Following ischemic insult or other traumatic injury to neuronal cells, a number of biochemical changes occur in neuronal tissue surrounding the injured region. Particularly relevant to the present invention, there is a rise in the extracellular concentration of the excitatory neurotransmitter glutamate. It is believed that this elevated glutamate level exacerbates the primary insult, possibly by acting at excitatory glutamate receptors, and that at least some of the excess glutamate results from enzymatic conversion of glutamine to glutamate by glutaminase (Newcomb, WO 99/09825). This high concentration of glutamate is believed to be an important factor in delayed neuronal death, in which the ischemic lesion increases approximately 2-fold over a period of time 2–72 hours following the initial ischemic insult. Newcomb also disclosed that glutamine hydrolysis remains associated with cell fragments after neuronal death, and showed that glutamate generation by glutaminase in damaged neurons was sufficient to account for glutamine toxicity in hypoxic neuronal/glial cells. As shown herein, the invention compounds are able to block pathological glutamate production in brain membranes and microglia, the major sources of glutamate production in damaged brain tissue.

A well-established in vivo model of cerebral ischemic damage (stroke) is the rat middle cerebral artery occlusion (MCAO) model in which a rat's middle cerebral artery is permanently occluded (Zea Longa et al.). Such test paradigms are used to assess the ability of test compounds to reduce neuronal damage in vivo. That is, using the MCAO model as an example, animals subjected to MCAO and fitted with a microdialysis probe in the affected brain region are given a test glutaminase inhibiting compound through the probe. Glutamate production is measured, as described above, and a compound is considered to be potentially neuroprotective if it attenuates the rise in glutamate in the ischemic penumbra region.

Further tests are made giving the test compound systemically, as this mode of administration is contemplated for use in the treatment of mammalian subjects. That is, a compound is given systemically, typically intravenously, to test animals who have undergone neuronal insult, such as ischemic insult to the central nervous system, as discussed above. The compound is administered in a pharmaceutically acceptable vehicle, preferably an aqueous vehicle, such as normal or buffered saline. For compounds with low aqueous solubility, suspensions of very fine particles have been employed. Selected brain regions are then assessed for presence of absence of neuronal damage, usually by any of a number of histological techniques known in the art. Direct administration to the affected region, such as by intracerebroventricular or intrathecal delivery routes or direct shunt, are also possible in the context of the present invention.

Dose-response studies, which are within the knowledge and judgement of skilled practitioner, can be used to establish adequate dosing ranges for experimental treatment paradigms, as well as to extrapolate such doses to use in larger animals, including humans.

C. Neuropsychiatric Disorders and other Disorders of Neuronal Signaling

The compounds of the invention may also be used for regulation of neurotransmission, i.e. in the treatment of neuropsychiatric disease. Glutaminase participates, directly or indirectly, in the biosynthesis of the major excitatory neurotransmitters of brain, glutamate and aspartate, and the main inhibitory neurotransmitter, γ-amino butyrate. Partial inhibition of glutaminase in intact nervous tissue may be used to modulate the balance of excitatory and inhibitory neurotransmission, and thus be of value in treating disorders of nervous system function which involve aberrant neuronal signaling. These disorders include pain, epilepsy, and neuropsychiatric disorders such as depression, anxiety and schizophrenia.

EXAMPLES

The following examples illustrate but are not intended in any way to limit the invention.

Example 1

Synthesis of SNX-1770 (Bis-2'-[5-(phenylacetamido)-1,3,4-thiadiazol-2-yl]ethyl sulfide)

Into a 1 L pear-shaped flask were place 9.1 g thiosemicarbazide ($H_2N(C=S)NHNH_2$), 8.9 g 3,3'-thiodipropionic acid (see FIG. 1), and 90 mL $POCl_3$. The resulting suspension was heated at 90° C. for 3 h, then cooled to room temperature and poured into 400 g of ice. The resulting mixture was filtered and then brought to pH 14. The white solid which formed was washed with 2×200 mL water and dried in vacuo at 50° C. to give 8 g bis-2'-(5-amino-1,3,4-thiadiazol-2-yl)ethyl sulfide (see FIG. 1). This product (4.32 g) was heated with 24 mL pyridine and 4.5 mL phenyl acetyl chloride until the mixture was homogeneous. The solution was cooled to room temperature and triturated with 50 mL methanol and filtered to give a crude solid. This solid was redissolved in 8 mL DMSO, 50 mL methanol was added, and the solution was allowed to sit at room temperature as the product crystallized. The product was collected and dried in vacuo at 50° C. to give approx. 1.5 g of the product SNX-1770.

Example 2

Glutaminase Inhibition: Cell Free Assay

A. Enzyme Preparation

Glutaminase gene-transfected SF9 cells were collected in a 50-mL polypropylene conical tube by centrifugation at 500×g for 10 min (Eppendorf Centrifuge 5810R, F34-6-38 rotor). The supernatant was discarded, and the cell pellet was stored at −80° C. For preparation of the lysate, the cells were thawed on ice and resuspended by pipetting in 0.8 mL cold lysis buffer with 0.5 mM 4-(2-aminoethyl)- benzenesulfonyl fluoride (AEBSF), a serine protease inhibitor. The suspension was stored in ice for 20 min, then subjected to two freeze-thaw cycles (liquid nitrogen followed by a room temperature water bath).

The volume of the cell homogenate was measured, and 1/3 volume of 1 M sucrose was added, to give a final concentration of 0.25 M sucrose. Aliquots 100 μL in volume were placed in 1.5 mL microtubes and stored at −80° C.

Alternatively, HEK (human kidney) cells were used. The medium was removed by aspiration, 5 mL PBS/1 mM EDTA was added, and the culture was incubate for 3 min to allow cells to detach. The cells were collected in a 50-mL conical tube using Eppendorf Centrifuge 5810R, F34-6-38 rotor, and spun at 200×g for 5 min. The supernatant was discarded, and the cell pellet was resuspended pipetting (approximately 0.12 g wet weight) in 0.3 mL lysis buffer with 0.5 mM AEBSF. The tube was left in ice for 20 min. The suspension was stored in ice for 20 min, then subjected to two freeze-thaw cycles as described above. Aliquots 100 μL in volume were placed in 1.5 mL microtubes and stored at −80° C.

The activity of the enzyme was determined colorimetrically. One unit of enzyme activity is defined as the amount of enzyme required to generate net OD 540nm=0.6 in a total reaction volume of 220 μL in one hour at room temperature.

B. Assay Procedure

Assay plates were prepared containing 2 μL test compound in DMSO/well. The enzyme was diluted to 1 unit (liver) or 0.8 unit (kidney)/100 μL in glutaminase assay buffer, and 100 μl diluted enzyme was added to each well of the assay plate by Multidrop (Labsystems). The contents were mixed by shaking at full speed for 1 min on TiterMix 100 (Brinkmann). The plates were preincubated at room temperature (RT) for 20 min to allow binding of test compounds to glutaminase, and 50 μL glutamine solution (7 mM in assay buffer) was added to each well by Multidrop. The contents were shaken at full speed for 30 sec on TiterMix 100 (Brinkmann), and the plates were then incubated at RT for 60 min (liver) or 90 min (kidney). To stop the reactions, 20 μL HCl (0.3 N) was added to each well by Multidrop and mixed immediately by shaking for 30 sec on TiterMix 100.

For quantification, glutamate (formed by glutaminase-catalyzed hydrolysis of glutamine) is oxidized to 2-oxoglutarate by a second enzyme, glutamate dehydrogenase (GDH), with the concomitant production of the reduced form of nicotinamide adenine dinucleotide (NADH). Reduction of nitro blue tetrazolium (NBT) in the assay solution by NADH, catalyzed by phenazine methosulphate (PMS), results in the formation of a blue-purple formazan. The absorption of formazan at 540 nm is linearly proportional to the concentration of glutamate up to 200 μM.

NBT/GDH reagent (50 μl) was added to each well by Multidrop and mixed by shaking for 30 sec on TiterMix 100, and the plates were incubated at RT for 20 min to allow color formation by the GDH reaction. Glutamate concentration was determined from formazan concentration as determined by reading OD540 nm on a SpectraMax 340.

Example 3
Inhibition of Glutaminase Activity in Rat Brain Membranes

Figure 2:
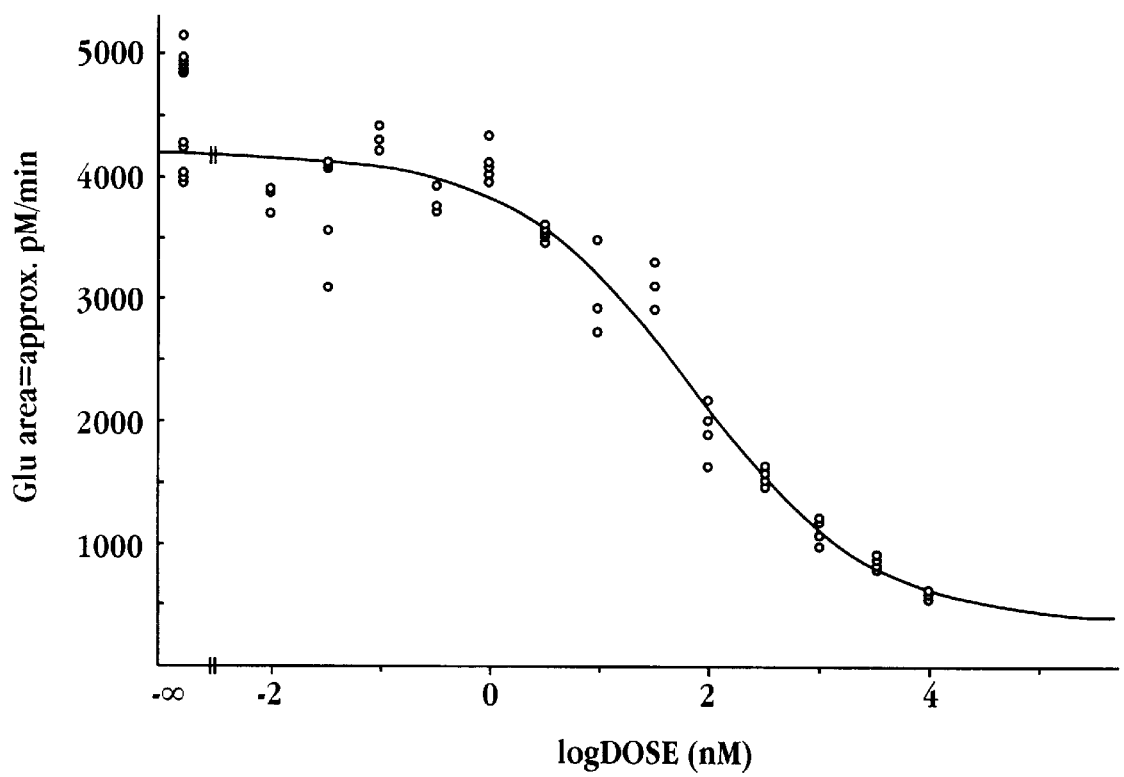
FIG. 2 shows inhibition of glutaminase activity in rat brain membranes ($PO_4^{-3}$ conc.=8 mM) by invention compound SNX-1770.

Rat brain membranes in 0.4 μL of 330 mM sucrose/20 mM tris (pH 8.6) were added to 40 μL of an aqueous solution containing glutamine, sodium phosphate, pH 8.6, and 5μL of SNX-1770 diluted from a 10 mM stock DMSO solution. The final assay concentrations were 5.7 mM glutamine; 1, 8 and 160 mM phosphate;, and 0.33 pM to 3.3 μM SNX-1770. Aliquots of 10 μL were removed at 0, 85, and 195 min, added to 90 μL 1:3 DMF/H$_2$O, and analyzed for glutamate by HPLC following derivatization with o-phthaldialdehyde and 2-mercaptoethanol (see Lo et al. 1998). Results are shown in FIG. 2.

Example 4
Effect of Glutamine on Glutamate Secretion by Microglial (BV2) Cells

Figure 3:
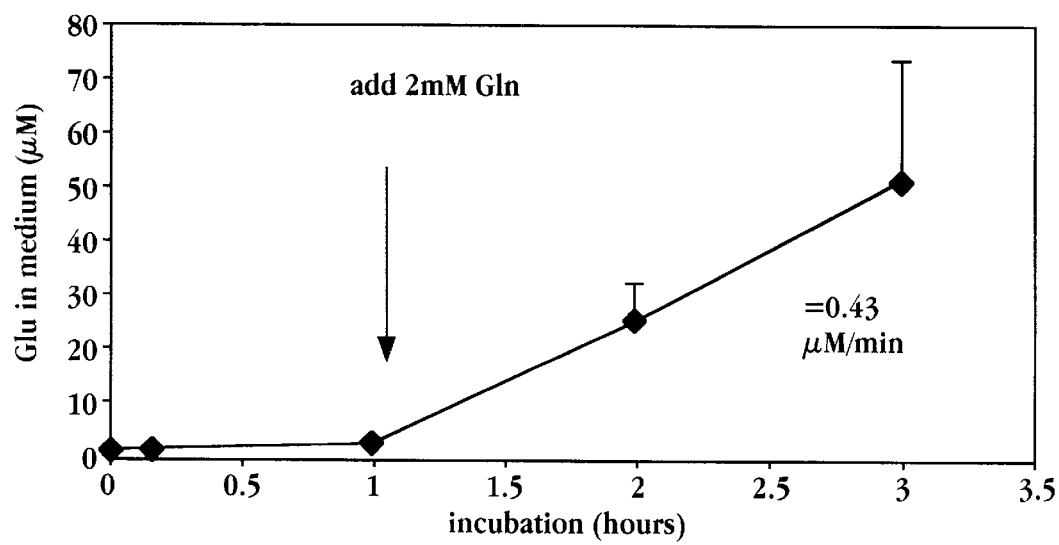
FIG. 3 shows the effect of glutamine on glutamate secretion into medium by microglial (BV2) cells.

BV-2 cells were cultured using Dulbeccos minimal essential medium containing 10% heat inactivated fetal bovine serum, and grown to 70–80% confluency before use. On the day of the experiment, cells were placed in glutamine free medium and aliquots removed for glutamate analysis at 0, 10 and 60 min. Glutamine was then added, and further aliquots removed for glutamate analysis, as above, at each of the next two hours. Results are shown in FIG. 3.

Example 5
Inhibition of Microglial Glutamate Secretion

BV-2 cells were cultured in 24 well plates using Dulbeccos minimal essential medium containing 10% heat inactivated fetal bovine serum, and grown to 70–80% confluency before use. On the day of the experiment, cells were placed in glutamine free medium for 1 to 1.5 hours. Glutamine and SNX-1770 (diluted from a 10 mM stock DMSO solution) were dissolved in glutamine free medium at two times the test concentration (i.e., 2 mM for glutamine). This solution was used to replace one half of the 0.5 mL culture medium volume at the end of the glutamine free incubation. Aliquots of 10 μL medium were removed at 2 h and 4 h and placed in 96 well microtiter plates with 90 μL DMF/water (1:9) for glutamate analysis. Results are shown in FIG. 4. Compound 1770 was able to inhibit glutamate efflux by microglia, giving an 1C$_{50}$ value of 80–120 nM and ca.85% inhibition at 10 μM.

Example 6
Effect of SNX-1770 on Intracelullar Amino Acids and Nucleotides in Intestinal Epithelial Cells Intestinal epithelial (CACO2) cells were grown in 12 well plates with Eagles minimal essential medium containing 2 mM glutamine, as recommended (American Tissue Culture Collection). When the cells reached about 80% confluency, fresh glutamine was added to 2 mM. SNX-1770 was diluted from a 100 μM stock in medium and added at concentrations varying from 10 nM to 10 μM. After 6.5 h of incubation, cultures were washed twice with phosphate buffered saline and extracted with 100 μL 1M perchloric acid. Extracts were neutralized with 30 μL of 5M potassium carbonate, centrifuged, and analyzed by HPLC for nucleotides, as described in Di Pierro et al. 1995, and for amino acids, as described in Lo et al. 1998. Results are shown in FIG. 5A (amino acids) and FIG. 5B (nucleotides).

FIG. 5A compares the effects of differing doses of SNX-1770 on glutamate, glycine and taurine in the extracts, showing a dose dependent decrease in glutamate, with no effect on glycine or taurine (data are n=3 analyses of 3 μL aliquots from independent extracts of independent culture wells, ±std. dev.). FIG. 5B shows analysis for nucleotides (n=1 analysis of pooled extracts from 3 culture wells exposed to control medium [top], or medium containing 10 μM SNX-1770).

Example 7
Effects of SNX-1770 on Intracellular Amino Acids in Primary Cultures of Cerebellar Granule Cells Primary cultures of cerebellar cortex were prepared in 6 well plates with 2.5 mL Dulbeccos minimal essential medium/horse serum, as described in A. Schousboe et al., 1989. At day 3, when cultures contained primarily the granule cell neurons, either 2.5 μL of DMSO or 10 mM SNX-1770 in DMSO (final concentration, 10 μM) was added to individual wells. After 5 h incubation, the cultures were washed twice with phosphate buffered saline, extracted with perchloric acid and analyzed for amino acids as described for FIG. 5A.

To produce dose response curves for lowering of intracellular Glu and Asp (FIG. 6A–B), the procedure was repeated with 4 days (for cerebellar granule cells) and 12 days of incubation (for astrocytes). A series of dilutions of SNX-1770 were made in DMSO, and these were added to 4 or 7 culture wells (at days 4 and 12, respectively), such that wells contained 0. 1% DMSO and/or concentrations of SNX-1770 from 10 nM to 10 μM. Results are shown in FIGS. 6A–B. Data are expressed as the ratio of Glu, Asp, or GABA to Ala (neurons and astrocytes) or Ser (astrocytes). (Amounts of Ala and Ser do not change with SNX-1770.)

While the invention has been described with reference to specific methods and embodiments, it will be appreciated that various modifications may be made without departing from the invention.

It is claimed:

1. A method of selectively inhibiting glutaminase in a cell or tissue, comprising administering to said cell or tissue an effective amount of a compound of formula I:

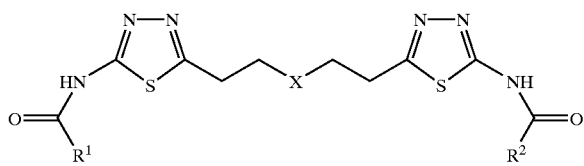

I where
X is sulfur or oxygen, and $R^1$ and $R^2$ are independently selected from the group consisting of lower alkyl, lower alkoxy, aryl, thiophenyl and —$(CH_2)_n$-aryl, where n is 0 or 1, and aryl is a monocyclic aromatic or heteroaromatic group, having ring atoms selected from the group consisting of carbon, nitrogen, oxygen, and sulfur, and having at most three non-carbon ring atoms, which group may be unsubstituted or substituted with one or more substituents selected from halogen, lower alkyl, lower alkoxy, amino, lower alkyl amino, amino (lower alkyl), or halo(lower alkyl).

2. The method of claim 1, wherein X is sulfur.

3. The method of claim 2, wherein each of $R^1$ and $R^2$ is —$(CH_2)_n$-aryl.

4. The method of claim 3, wherein each of $R^1$ and $R^2$ is 2-thiophenyl.

5. The method of claim 3, wherein each of $R^1$ and $R^2$ is 2-furanyl.

6. The method of claim 3, wherein each of $R^1$ and $R^2$ is phenyl or benzyl, unsubstituted or substituted with lower alkyl or lower alkoxy.

7. The method of claim 6, wherein each of $R^1$ and $R^2$ is benzyl.

8. The method of claim 6, wherein each of $R^1$ and $R^2$ is p-methoxy phenyl.

9. The method of claim 6, wherein each of $R^1$ and $R^2$ is m-tolyl.

10. The method of claim 1, wherein each of $R^1$ and $R^2$ is lower alkoxy.

11. The method of claim 10, wherein each of $R^1$ and $R^2$ is ethoxy.

12. The method of claim 1, wherein each of $R^1$ and $R^2$ is lower alkyl.

13. The method of claim 12, wherein each of $R^1$ and $R^2$ is t-butyl.

14. The method of claim 1, wherein said tissue is neuronal tissue having been subjected to ischemia, physical trauma, or a neurodegenerative disorder.

15. The method of claim 1, wherein the tissue is intestinal tissue.

* * * * *